United States Patent [19]

Arima et al.

[11] 4,025,788

[45] May 24, 1977

[54] RADIOMETRIC ANALYZER

[75] Inventors: Sumitaro Arima, Sendai; Minoru Oda; Kyoichi Miyashita, both of Amagaski; Mamoru Takada, Amagasaki, all of Japan

[73] Assignees: Tohoku Electric Power Company, Inc.; Mitsubishi Denki Kabushiki Kaisha, Tokyo, both of Japan

[22] Filed: Feb. 5, 1976

[21] Appl. No.: 655,490

Related U.S. Application Data

[63] Continuation-in-part of Ser. No. 569,143, April 17, 1975, abandoned, which is a continuation of Ser. No. 432,235, Jan. 10, 1974, abandoned.

[30] Foreign Application Priority Data

Jan. 18, 1973  Japan .................................. 48-8100

[52] U.S. Cl. .................................. 250/253; 250/336
[51] Int. Cl. ........................................ G01v 5/00
[58] Field of Search .......... 250/253, 269, 336, 364, 250/428, 432, 435

[56] References Cited

UNITED STATES PATENTS 3,622,795  11/1971  Dorman, Jr. et al. ......... 250/432 X

*Primary Examiner*—Davis L. Willis
*Attorney, Agent, or Firm*—Oblon, Fisher, Spivak, McClelland & Maier

[57] ABSTRACT

A radiometric analyzer for measuring the characteristic values of a sample by radiation includes a plurality of radiation measuring subsystems having different ratios of sensitivities to the elements of the sample and linearizing circuits having inverse function characteristics of calibration functions (calibration function while varying the density in a constant content ratio of the sample) which correspond to the radiation measuring subsystems and a weighing adder for operating a desirable linear combination of the outputs of the linearizing circuits and operators for operating between two or more different linear combinations.

4 Claims, 6 Drawing Figures

RADIOMETRIC ANALYZER

CROSS REFERENCE TO RELATED APPLICATIONS

This application is a continuation-in-part of Ser. No. 569,143 filed Apr. 17, 1975 and now abandoned which in turn is a continuation of Ser. No. 432,235 filed Jan. 10, 1974, now abandoned.

A typical radiometric analyzer comprises three radiation measuring subsystems using a gamma ray source ($E\gamma > 50$ KeV), a soft X-ray source ($E_x \simeq 20$ KeV) and a neutron source as radiation sources whereby the density of hydrocarbons, e.g., heavy oils, the sulfur content and the calorific value may be calculated.

BACKGROUND OF THE INVENTION

1. Field of the Invention

This invention relates to a radiometric analyzer for precisely measuring by radiation the various characteristic values of a sample.

2. Description of the Prior Art

Radiometric analyzers for measuring characteristic values of a sample by radiation are known. However, in such analyzers, the calibration of measuring error dependent upon the difference of content ratio of the sample is not realized or is incomplete. The error depending upon the difference of content ratio of the sample is, for example, error due to the CH ratio in the case of measuring the density of hydrocarbons by gamma ray densitometer.

When the density of hydrocarbons is measured by utilizing the absorption of gamma rays, it is preferable that the degrees of absorption of the gamma rays by carbon and hydrogen are proportional to the masses of carbon and hydrogen. In practice, however, the mass absorption coefficient of gamma rays per mass of hydrogen is about two times higher than that of carbon. Accordingly, the mass of hydrogen is erroneously overestimated. This error is referred to as error due to the CH ratio.

In the conventional technology for overcoming this error, there is a method of using an X-ray source or a gamma ray source having specific energy to provide equal mass absorption coefficients of carbon and hydrogen (about 20 KeV). In this case, 241 Am—Ag, 147 Pm—Al and the like are used as the ray sources. However, this is not completely monochromatic with the result that the energy spectrum is disadvantageously varied by absorption depending upon the sample and the effective energy is undesirably varied.

SUMMARY OF THE INVENTION

It is therefore an object of the present invention to provide a radiometric analyzer for measuring the characteristic values such as the density of a sample and the contents of elements of the sample etc. by radiation under a decreasing error caused by the content ratio of the elements of the sample.

The foregoing and other objects are attained in accordance with one aspect of the present invention, through the provision of a radiometric analyzer comprising a plurality of radiation measuring subsystems having different ratios of sensitivities to elements of the sample preferably in the same number as the elements of the sample, linearizing circuits having inverse function characteristics of calibration functions (calibration function while varying the density in a constant content ratio of the sample) which correspond to the radiation measuring subsystems, a weighing adder for obtaining desirable linear combination of the outputs of the linearizing circuits and one or more operators for operating between two or more different linear combinations of the output signals of the weighing adders.

The radiation measuring subsystem comprises a radiation source, a sample vessel, a radiation detector and a detecting circuit. When the detector is an ionizing chamber, a current sensitive amplifier may be utilized for the detecting circuit. When the detector is a radiation counter, a detecting pulse amplifier, a discriminator and a count rate meter may be utilized. The discriminator can be replaced by a single channel pulse height analyzer depending upon the types of the radiation sources.

The radiation measuring subsystem receives absorbed or scattered radiation depending upon the sample so as to generate a voltage signal proportional to the intensity. The linearizing circuits linearize nonlinearity of the calibration functions which are specific to the subsystems to be linearized. As a result, the output voltages become linear combination of the contents of the elements of the sample per unit volume (g/cm$^3$).

With regard to the linear combinations realized for each of the subsystems, the ratio of the coefficients to the elements is different in each of the subsystems. They are respectively the linear combination. The value can not be directly used for the measurement because the ratio of the coefficient is different from the ratio of the coefficient to the object measured value such as the density.

The weighing adder operates the linear combination of the output voltages of the linear calibration circuits. As a result, it forms a new linear combination for a content per unit volume of the elements of the sample.

The weighing coefficients of the weighing adder are selected so as to provide the same coefficients for the objective measured value. (For example they are "1"s in the case of the density). If necessary, an operator is connected to perform addition, subtraction, multiplication and division between the different linear combinations to obtain another objective measured value.

The radiometric analyzer of the invention can be used for analysis of various samples. As one example, a radiometric analyzer for measuring the density, the sulfur content and the calorific value of hydrocarbon will be described.

The structure of the analyzer comprises radiation measuring subsystems; one for measuring the absorption of gamma rays by the sample, one for measuring the absorption of X-rays by the sample and one for measuring the thermal neutrons produced by irradiating fast neutrons to the sample. For the linear calibration circuits, there is provided a logarithmic amplifier for the gamma ray absorption meter; a logarithmic amplifier for the X-ray absorption meter and an offsettable linear amplifier for the neutron meter.

The density, the calorific value and the sulfur content per unit volume (W/V) are calculated by the linear combinations from outputs of the linear calibration circuits. The weight content of sulfur (W/W) is calculated by dividing the sulfur content per unit volume by the density of the sample. The calorific value of the sample can be calculated with high accuracy by the linear combination of the volume contents (W/V) of the elements of the sample.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

DETAILED DESCRIPTION OF THE PREFERRED EMBODIMENTS

Figure 1:
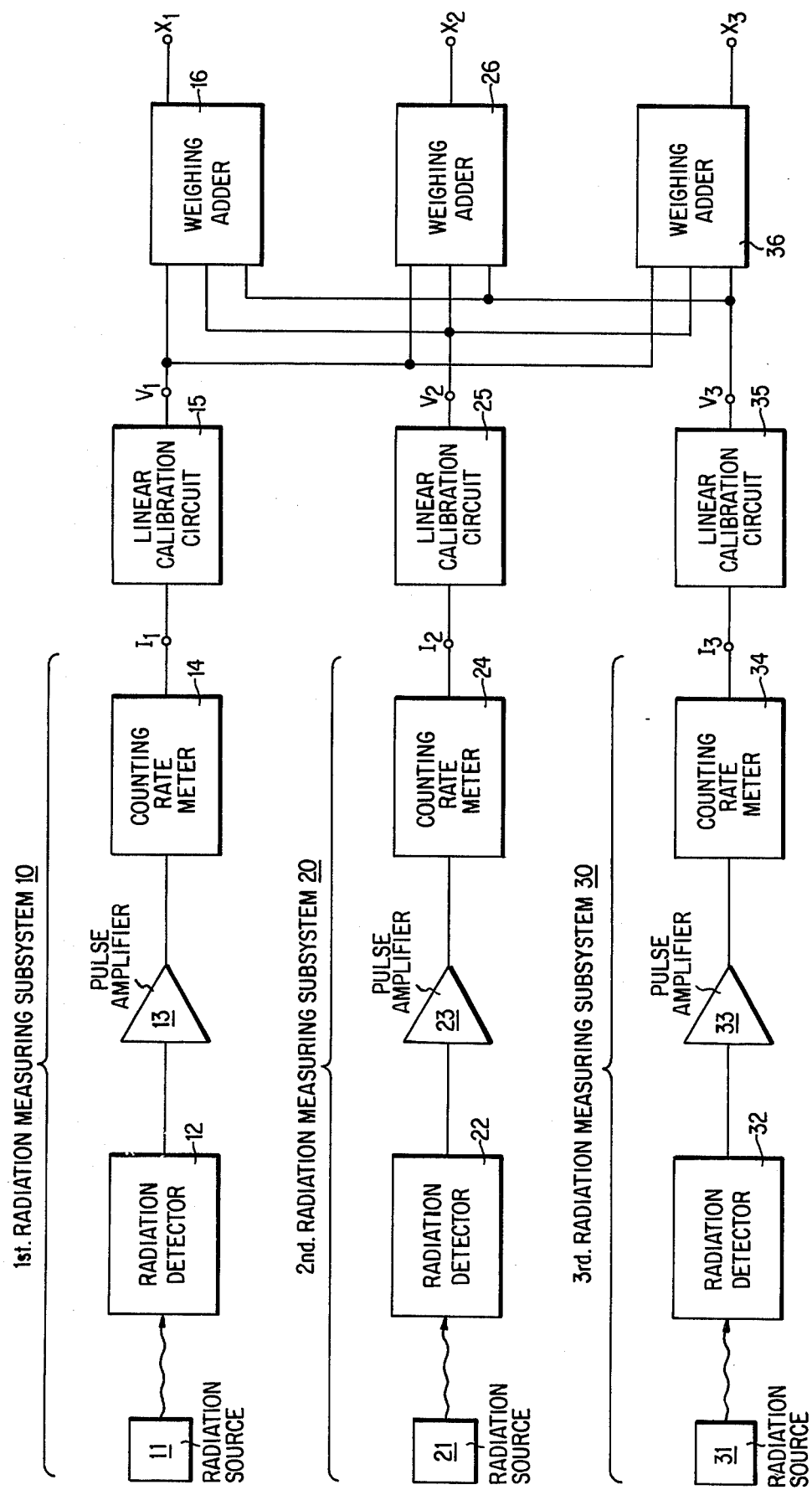
FIG. 1 is a block diagram showing the principles of operation of a preferred embodiment of the apparatus according to the present invention.

Referring now to the drawings, wherein like reference numerals designate identical or corresponding parts throughout the several views, and more particularly to FIG. 1 thereof, there is shown a block diagram illustrative of the principles of operation of the radiometric analyzer of the present invention wherein the sample to be measured is assumed to be made of three elements. The characteristic values for measurement are the contents of the elements of the sample per unit of volume.

In the drawings, the analyzer comprises first, second and third radiation measuring subsystems 10, 20, 30; radiation sources 11, 21, 31; radiation detectors 12, 22, 32; pulse amplifiers 13, 23, 33; count rate meters 14, 24, 34; linearizing circuits 15, 25, 35; and weighing adders 16, 26, 36. The subsystems 10, 20, 30 should be selected so that the subsysytems have different ratios of sensitivities to elements of the sample.

The radiations of the radiation sources 11, 21, 31 are absorbed or scattered by the sample in a vessel for the sample (not shown). The intensities of the incident radiation to the detectors 12, 22, 32 are converted to the output voltages $I_1$, $I_2$, $I_3$ of the count rate meters 14, 24, 34. The count rate meter usually comprises a discriminator, and, if desirable, a single channel pulse height analyzer.

In FIG. 1, radiation counters are considered for the detectors 12, 22, 32. However, when the detectors are ionizing chambers, the count rate meters are not needed and the pulse amplifiers should be replaced by current amplifiers. The output voltages $I_1$, $I_2$, $I_3$ of the subsystems can be given by the following equations:

$$I_1 = f_1 (a_{11} X_1 + a_{12} X_2 + a_{13} X_3), \quad (1)$$

$$I_2 = f_2 (a_{21} X_1 + a_{22} X_2 + a_{23} X_3), \text{ and} \quad (2)$$

$$I_3 = f_3 (a_{31} X_1 + a_{32} X_2 + a_{33} X_3), \quad (3)$$

wherein $X_1$, $X_2$, and $X_3$ represent masses of elements of the sample per unit of volume (g/cm³); $f_1$, $f_2$ and $f_3$ represent calibration functions of the three subsystems and $a_{11}, \ldots a_{33}$ represent sensitivity coefficients of the three subsystems to the elements.

When gamma ray absorption measurement is considered, the calibration function f is an exponential function as is well known. In this case, a mass absorption coefficient corresponds to the sensitivity coefficient $a$.

The linearizing circuits 15, 15, 35 respectively have inverse function characteristics to $f_1, f_2, f_3$, which are respectively linearized by the following equations to give the outputs $V_1$, $V_2$, $V_3$.

$$V_1 = f_1^{-1}(I_1) = a_{11}X_1 + a_{12}X_2 + a_{13}X_3 \quad (4)$$

$$V_2 = f_2^{-1}(I_2) = a_{21}X_1 + a_{22}X_2 + a_{23}X_3 \quad (5)$$

$$3 V_3 = f_3^{-1}(I_3) = a_{31}X_1 + a_{32}X_2 + a_{33}X_3 \quad (6)$$

The weighing adders 16, 26, 36 operate linear combinations of the outputs $V_1$, $V_2$, $V_3$ to calculate the object characteristic values $X_1$, $X_2$, $X_3$.

$$A_{11}V_1 + A_{12}V_2 + A_{13}V_3 = X_1 \quad (7)$$

$$A_{21}V_1 + A_{22}V_2 + A_{23}V_3 = X_2 \quad (8)$$

$$A_{31}V_1 + A_{32}V_2 + A_{33}V_3 = X_3 \quad (9)$$

$$A_{11}a_{11} + A_{12}a_{21} + A_{13}a_{31} = 1 \quad (7a)$$
$$A_{11}a_{12} + A_{12}a_{22} + A_{13}a_{32} = 0 \quad (7b)$$
$$A_{11}a_{13} + A_{12}a_{23} + A_{13}a_{33} = 0 \quad (7c)$$
$$A_{21}a_{11} + A_{22}a_{21} + A_{23}a_{31} = 0 \quad (8a)$$
$$A_{21}a_{12} + A_{22}a_{22} + A_{23}a_{32} = 1 \quad (8b)$$
$$A_{21}a_{13} + A_{22}a_{23} + A_{23}a_{33} = 0 \quad (8c)$$

wherein $A_{11}$, $A_{12}$ and $A_{13}$ represent roots of the simultaneous linear equations 7a, 7b, 7c; $A_{21}$, $A_{22}$ and $A_{23}$ represent roots of the simultaneous linear equations 8a, 8b, 8c; and $A_{31}$, $A_{32}$ and $A_{33}$ are the same as stated.

In accordance with the invention, the contents of elements of the sample per unit volume $X_1$, $X_2$, $X_3$ can be precisely calculated. Moreover, effective characteristic values can be calculated from the combinations of the object characteristic values $X_1$, $X_2$, $X_3$ by adding simple operation circuits.

For example, the addition of the outputs of the weighing adders 16, 16, 36 give the density of the sample. When a measurement of density is required, it is enough to give one for each of all the values of the right side of the equations 7a, 7b, 7c by determining the weighing coefficients $A_{11}$, $A_{12}$, $A_{13}$ of the weighing adders 16. This is quite economical.

In accordance with the structure of the invention, the characteristic values of combination of the contents of elements of the sample per unit volume can be precisely calculated and the error due to the content ratio which is found in the conventional analyzer can be completely removed.

A radiometric analyzer for hydrocarbon analysis according to the invention will now be illustrated in detail with reference to FIG. 2. The analyzer therein depicted measures the density, sulfur content, and calorific value of heavy oil, which is a sulfur containing hydrocarbon. The density and sulfur content can be precisely measured by the radiometric method but the calorific value (per unit of weight) is indirectly measured from the content ratio of elements of the material.

Figure 2:
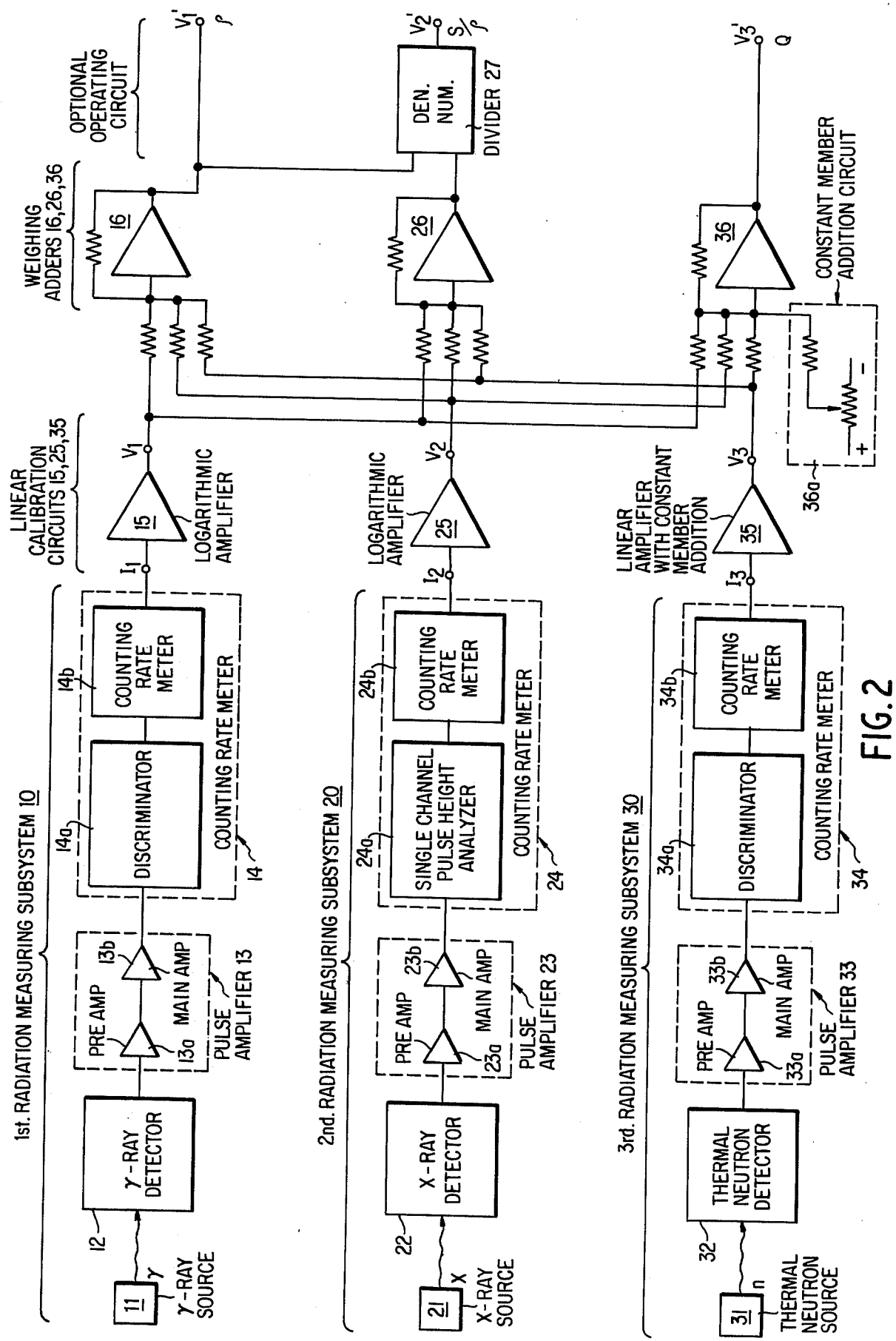
FIG. 2 is a block diagram showing a preferred embodiment of a radiometric analyzer used for hydrocarbon analysis according to the present invention.

In the radiation measuring subsystem 10 of FIG. 2, the reference numeral 11 designates a γ-ray source, and 12 designates a γ-ray detector, e.g. a proportional radiation counter for γ-ray measurement. In the second subsystem 20, the reference numeral 21 designates an X-ray source, and 22 designates an X-ray detector, e.g. a proportional radiation counter for X-ray measurement. In the third subsystem 30, the reference numeral 31 designates a thermal neutron source and 32 designates a thermal neutron detector, e.g. a BF$_3$ radiation counter.

The first subsystem 10 provides an output signal which is approximately proportional to the density since the mass absorption coefficient of γ-rays having higher than several tens of KeV of energy is approximately constant independent of the absorption material. As examples of suitable γ-ray sources, 241Am (60 KeV), $^{137}$Cs(662KeV), or the like, can be used. However, the mass absorption coefficients of atoms of the sample are not strictly equal. Accordingly, it is difficult to precisely determine the density by using only the first subsystem 10, and hence it becomes necessary to provide the compensation operation using the output signals of the other subsystems.

The second subsystem 20 provides an output signal which is approximately proportional to the sulfur content per unit of volume by using the absorption of X-rays having about 20 KeV of energy. For example, the mass absorption coefficient of sulfur exposed to X-rays having about 17 KeV is about 20 times that of other elements, so that the output of such a subsystem is especially sensitive to sulfur. As an example of a suitable X-ray source, $^{241}$AM(17 KeV) can be used. In the system, it becomes necessary to provide the calibration operation by using the output signal of the other subsystem, the same as in the density case explained above.

The third subsystem 30 provides a signal which is approximately proportional to the hydrogen content per unit of volume by using the scattering and slowing of high speed neutrons. Hydrogen has substantially the same mass as that of neutrons, so that the slowing effect achieved by elastic scattering is particularly high, without being effected by the other elements. As the neutron source, $^{241}$Am—Be or Ra—Be, for example, may be used.

Referring once more to the first subsystem 10, it is seen to comprise an amplifier 13 consisting of a pre-amplifier 13a and a main-amplifier 13b, a counting rate meter 14 consisting of a discriminator 14a and a counting rate meter 14b, a logarithimic amplifier 15 operating as a linearizing circuit and a weighing adder 16.

The second subsystem 20 comprises an amplifier 23 consisting of a preamplifier 23a and a main-amplifier 23b, a counting rate meter 24 consisting of a discriminator 24a and a counting rate meter 24b, a logarithmic amplifier 25 operating as a linearizing circuit and a weighing adder 26 and a divider 27.

The third subsystem 30 is seen to similarly comprise an amplifier 33 including a pre-amplifier 33a and a main-amplifier 33b, a counting rate meter 34 which consists of a discriminator 34a and a counting rate meter 34b, a linear amplifier with a constant member addition 35 (offsettable amplifier) operating as a linearizing circuit and a weighing adder 36a and a constant member addition circuit 36b.

The discriminators 14a and 34a of the first and third subsystems 10 and 30 are conventional discriminators. However, the discriminator 24a of the second subsystem 20 comprises a single channel pulse height analyzer. When $^{241}$Am is used, only pulses based on X-rays having 17 KeV will be encountered.

If the elements of heavy oil are presumed to comprise the elements carbon, hydrogen, and sulfur, and the masses of carbon, hydrogen and sulfur per unit of volume are represented as C, H, S(W/V), the pulse counting rates of each subsystem can be mathematically represented as follows:

$$I_1 = I_{01} \exp\{-(\mu_c C + \mu_s S + \mu_H H)\} d_1 \quad (11)$$

$$I_2 = I_{02} \exp\{-(\mu_c' C + \mu_s' S + \mu_H' H)\} d_2 \quad (12)$$

$$I_3 = \alpha C + \beta S + \gamma H + \delta \quad (13)$$

wherein $I_{01}$ and $I_{02}$ represent the count rate with no sample; $\mu, \mu'$ represent the mass absorption coefficient ($C$, $S$ and $H$ represent carbon, sulfur, and hydrogen, respectively), and $d_1$ and $d_2$ represent the thickness (g/cm$^2$) of the sample. The values of $\alpha, \beta, \gamma$ and $\delta$ are constants which depend upon the neutron velocity reducing efficiency of the elements and the size of the sample. The respective pulse signals are converted to a voltage proportional to the count rate by the counting rate meters 14, 24 and 34, respectively.

The following linearized voltages are provided by the logarithmic amplifiers 15 and 25 based on the pulse count rates $I_1$ and $I_2$ and by the intercept additional linear amplifier 35 (offsettable amplifier) based on the pulse count rate $I_3$, respectively:

$$V_1 = (\mu_c C + \mu_s S + \mu_H H) \quad (14)$$

$$V_2 = (\mu_c' C + \mu_s' S + \mu_H' H) \quad (15)$$

$$V_3 = (\alpha C + \beta S + \delta H) \quad (16)$$

The equations 14, 15, 16 relate to typical examples of the equations 4, 5, 6.

In equation 14, $V_1$ is a voltage which is approximately proportional to the density, since the values $\mu_c, \mu_s$ and $\mu_H$ are substantially the same. In equation 15, $V_2$ is a voltage which is substantially proportional to the sulfur content, since the value of $\mu_s'$ is markedly higher than $\mu_c'$ and $\mu_H'$. In equation 16, $V_3$ is a voltage which is approximately proportional to the hydrogen content, since the values $\alpha, \beta$ are markedly lower than $\gamma$.

However, the above relationships are only an approximation, and, accordingly, a voltage which is precisely proportional to the object measuring value may be calculated by the operations. In the weighing adders 16, 26 and 36, the following operations are provided:

$$V_1' = (b_{11}V_1 + b_{12}V_2 + b_{13}V_3) \quad (17)$$

$$V_2' = (b_{21}V_2 + b_{22}V_2 + b_{23}V_3)/V_1' \quad (18)$$

$$V_3' = (b_{31}V_1 + b_{32}V_2 + b_{33}V_3 = b_0) \quad (19)$$

wherein $b_{11}, b_{12} \ldots b_{33}$ and $b_0$ are roots of the following simultaneous linear equations.

$$b_{11}\mu_c + b_{12}\mu_c' + b_{13}\alpha = 1 \quad (17a)$$

$$b_{11}\mu_s + b_{12}\mu_s' + b_{13}\beta = 1 \quad (17b)$$

$$b_{11}\mu_H + b_{12}\mu_H' + b_{13}\gamma = 1 \quad (17c)$$

$$b_{21}\mu_c + b_{21}\mu_c' + b_{21}\alpha = 0 \quad (18a)$$

$$b_{22}\mu_s + b_{22}\mu_s' + b_{23}\beta = 1 \quad (18b)$$

$$b_{23}\mu_H + b_{23}\mu_H' + b_{23}\gamma = 0 \quad (18c)$$

$$b_{31} = l \quad (19a)$$

$$b_{32} = m \quad (19b)$$

$$b_{33} = n \quad (19c)$$

$$b_0 = k \tag{19d}$$

Accordingly, the final output voltages can be represented as follows:

$$V_1' = (C + S + H) = K_1''\rho \tag{20}$$

$$V_2' = S/(C + S + H) = K_2''S/\rho \tag{21}$$

$$V_3' = (K + lC + mS + nH) = K_3''Q \tag{22}$$

$\rho$ = density of sample $S/\rho$ = sulfur content of sample $Q$ = calorific value wherein the constants $k$, $l$, $m$, and $n$ of equation (23) are determined experimentally so as to provide maximum correlation with the calorific value. For example, the ranges of $k$, $l$, $m$ and $n$ which provide the desirable correlation with respect to the example are:
$10,000 < k < 15,000$; $-5,000 < l < -3,000$; $-10,000 < m < -5,000$ and $3,000 < n < 8,000$.

As stated above, in accordance with the system of the present invention, a compensation function necessary for an increase in required accuracy can be precisely determined whereby measured values having extremely high accuracy can be provided. The physical meaning (dimensions) of the operation outputs are also clear.

The system according to the present invention requires subsystems which are the same in number as the number of elements of the heavy oil (carbon, hydrogen and sulfur) with respect to each value measured. However, it is unnecessary to provide more subsystems than those values to be measured. Accordingly, the system of the invention in calculating three values, i.e. density, sulfur content and calorific value, from three subsystems can be quite economical.

The calorific value of heavy oil can be measured from a density [$\rho$ (W/V)], a hydrogen content [H (W/V)] per unit of volume, or a hydrogen content [H (W/V) / $\rho$ (W/V)] per unit of weight. However, it has been found that the system of the present invention is superior to the conventional methods.

In the foregoing embodiments, the radiation is detected in a digital manner and the operation is carried out in an analogue manner. However, a digital technique and an analogue technique can be applied to the detection of the radiation and the operation. The analogue technique may be modified to mutually decrease drift by applying bias.

The advantages of the present invention can also be provided by replacing a portion of the plurality of subsystems connected to a certain detector other than a radiation detector.

Figure 3:
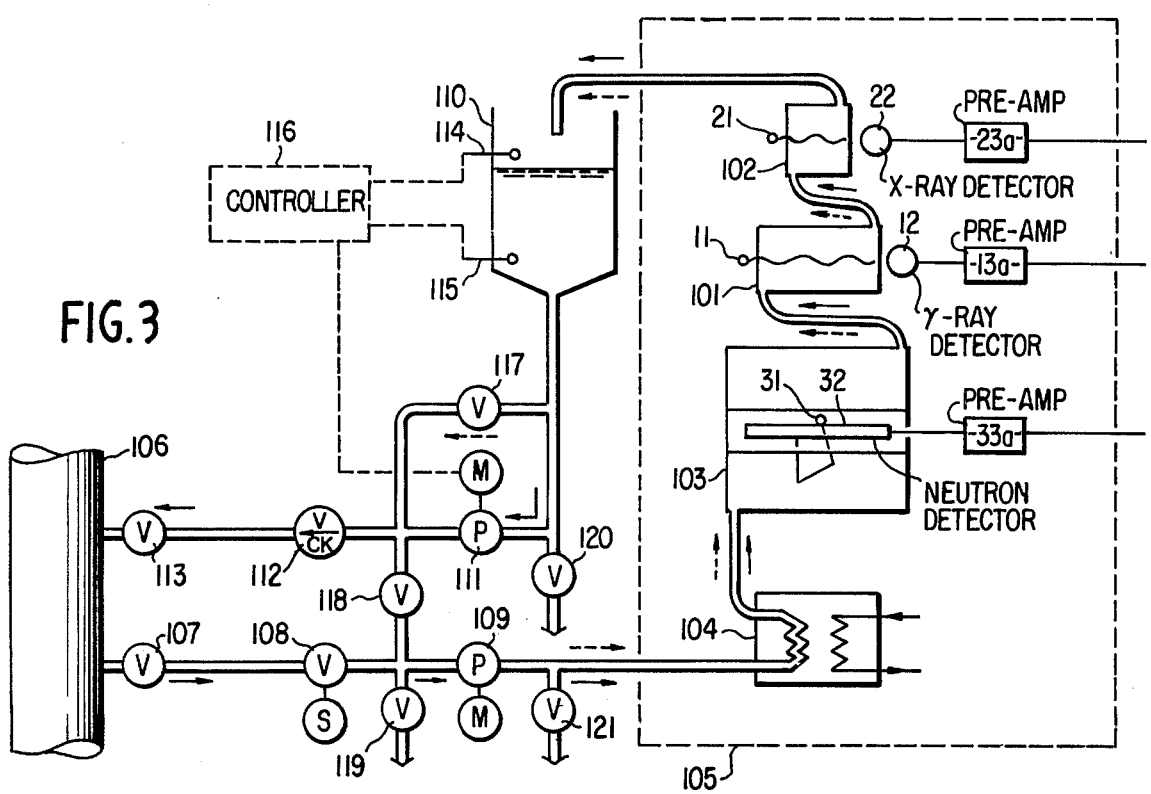
FIG. 3 is a schematic view showing an enlarged part of a sample vessel and other related parts of the radioactive analyzer used for hydrocarbon analysis according to the present invention.

FIG. 3 is a schematic view of a sample vessel and related parts of a radioactive analyzer for hydrocarbon analysis according to the present invention. In the embodiment therein depicted, it is possible to use an on-line measurement for continuously measuring the heavy oil passing through a pipe and to use a batch measurement for measuring each sample of heavy oil. Referring specifically to FIG. 3, the reference numeral 101 designates a sample vessel for $\gamma$-ray measurements, 11 designates a $^{241}$Am-$\gamma$-ray source, 12 designates a $\gamma$-ray detector, 13a designates a pre-amplifier, 102 designates a sample vessel for X-ray measurements, 21 designates a $^{241}$Am-X-ray source, 22 designates an X-ray detector, 23a designates a pre-amplifier, 103 designates a sample vessel for neutron measurement, 31 designates a $^{241}$Am-Be neutron ray source, 32 designates a neutron detector, 33a designates a pre-amplifier, and 104 designates a heat-exchange which is equipped for heating the heavy oil fed into the sample vessel to a predetermined temperature so as to eliminate the necessity of calibrating the temperature fluctuation and to maintain a stable measurement.

The above-described parts are maintained in a constant temperature case 105 which is kept at a temperature the same as that of the heated heavy oil temperature, e.g. 50° C, so as to maintain the stability of the radiometric analyzer. The flow of the heavy oil during the measurement of the heavy oil passing through a heavy oil pipe 106 in the on-line system is indicated by the solid arrows in FIG. 3. The heavy oil sample in the pipe 106 is passed through a valve 107, an electromagnetic valve 108, a constant flow pump 109, the heat-exchanger 104 and is radiometrically measured in the sample vessels 103, 101 and 102. The heavy oil sample is then fed to the storage tank 110 at atmospheric pressure. Thereafter, the heavy oil sample is fed by a pump 111 through a check valve 112 and a valve 113 back to the pipe 106. The operation of the pump 111 is controlled by a controller 116 according to the signals of conventional level detectors 114 and 115.

The flow of heavy oil during the measurement of the sampled heavy oil by the batch technique is indicated by the broken arrows in FIG. 3. The heavy oil sample is fed to the storage tank 110 and is passed through the valves 117 and 118, a constant flow pump 109, and heat-exchanger 104 to the sample vessels 103, 101 and 102 and is returned to the storage tank 110. Valves 119, 120 and 121 are used for discharging the heavy oil sample after the measurement. Thus, the density, the sulfur content, and the calorific value of the heavy oil sample are measured by the analyzer shown in FIGS. 2 and 3. The measured values from the analyzer of the present invention are compared with the measured values according to the analysis of the Japanese Industrial Standard wherein the density is measured by the hydrometer I method; the sulfur content is measured by the quartz tube-oxygen method; and the calorific value is measured by a B-type calorimeter.

Figure 4:
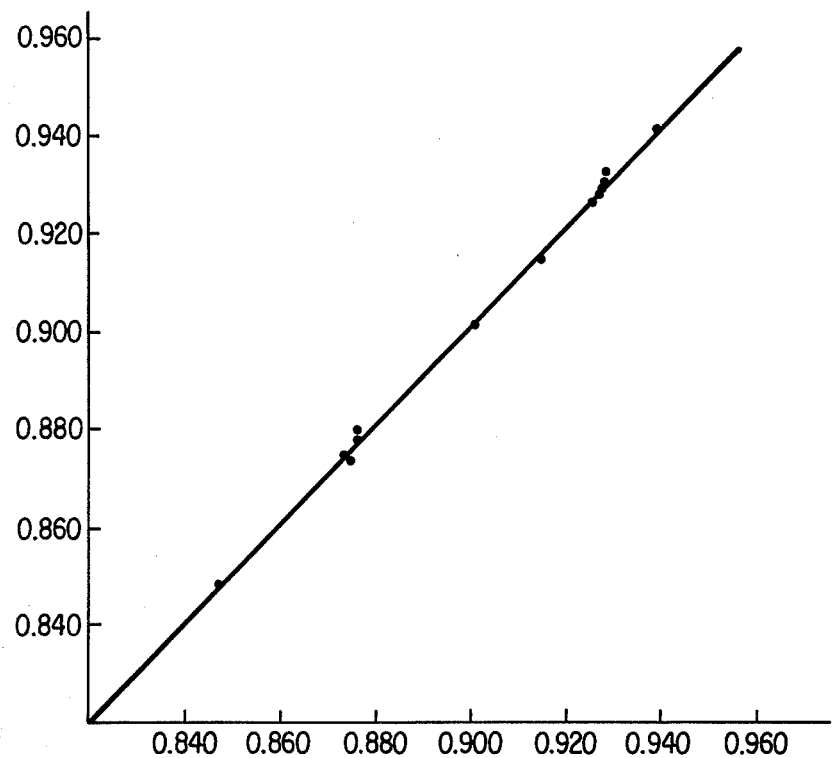
FIGS. 4, 5 and 6 are graphs showing the mutual relationships of the density, the content of sulfur, and the calorific value of heavy oil to values as measured by the Japanese Industrial Standard.
Figure 5:
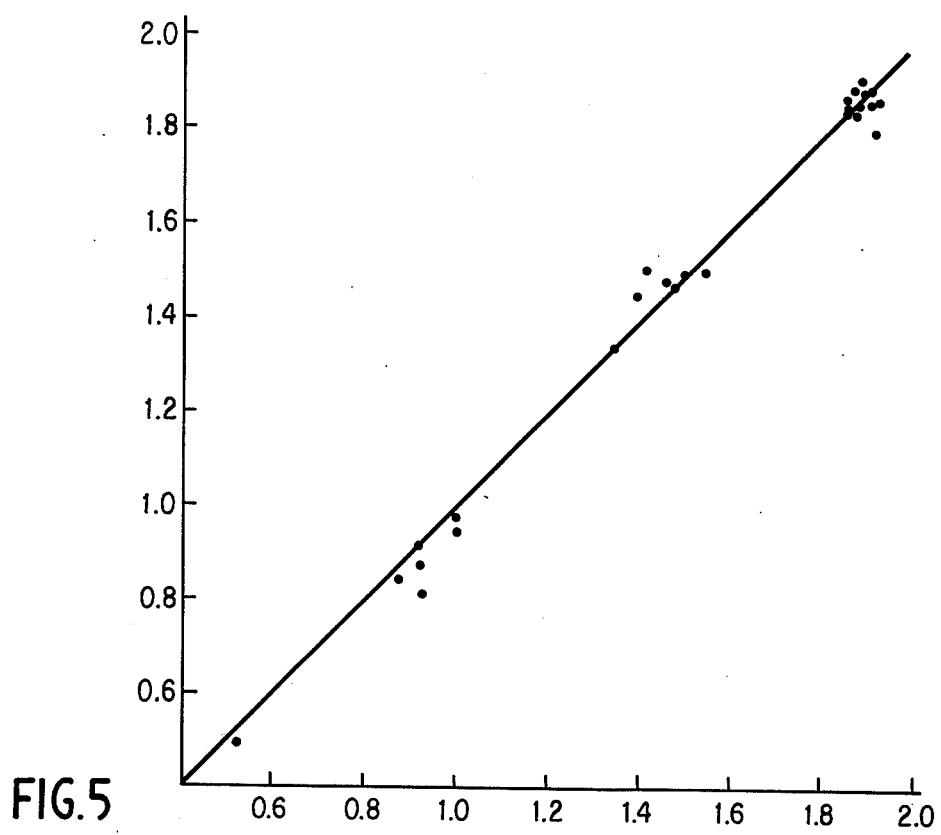
Figure 6:
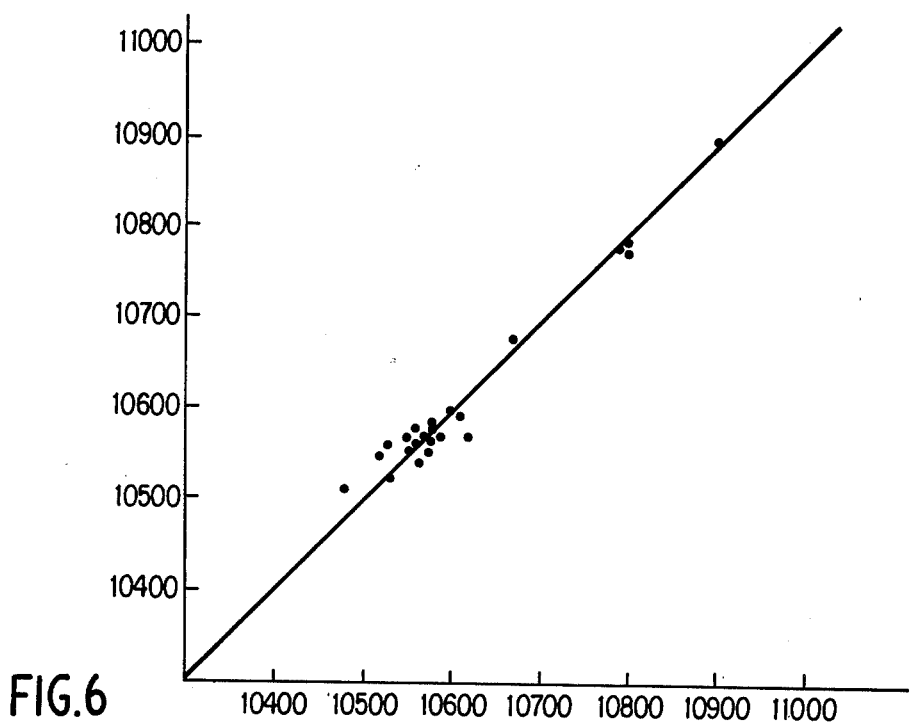

FIGS. 4, 5 and 6 show measured results of the density, sulfur content and calorific value of about 30 types of heavy oils, wherein the measured values from the analyzer of the invention are seen to be well correlated with the measured values by direct analysis, and wherein the standard deviations between the two techniques are respectively 0.008 (g/cm$^3$), 0.019 (%), and 17 (Kcal/kg).

It is clear from the foregoing that precise measurements are provided by the analyzer of the present invention. In the Japanese Industrial Standard, the allowable error of sulfur content measured by the same apparatus and the same person is 0.12 (%). Accordingly, the accuracy of the analyzer of the present invention is quite high. The accuracy can be further increased by improving the measuring system.

In the foregoing embodiment, the measurement of the characteristics of heavy oil have been illustrated. However, the fundamental features of the invention can be applied to the measurement of hydrocarbons and other various solid and liquid materials, as well as heavy oil.

As stated in detail above, the present invention measures various characteristics of a material with high accuracy by a rational calibration system to change of formula of the material in the radiometric analyzer.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A radiometric analyzer for measuring the characteristic values of a material by radiation comprising:
   a plurality of radiation measuring subsystems having different ratios of sensitivities to each of the elements of the material;
   the pluraliity of radiation measuring subsystems being equal in number to the elements of the material;
   linearizing circuits connected to each of the subsystems for calibrating nonlinear calibration functions of the subsystems to measure linear combinations of the contents of the elements of the material per unit volume from outputs of the subsystems; and
   weighing adders for operating the linear combinations of the outputs of the linear calibration circuits.

2. A radiometric analyzer for measuring the contents of elements of a material per unit volume by radiation comprising:
   a plurality of radiation measuring subsystems being equal in number to the elements of the material having different ratios of sensitivities to each of the elements of the material;
   linearizing circuits connected to each of the subsystems for linearizing nonlinear calibration functions of the subsystems to measure linear combinations of the contents of the elements of the material per unit volume from outputs of the subsystems; and
   weighing adders for operating the linear combinations of the outputs of the linearizing circuits, the number of the weighing adders being equal to the number of kinds of elements of the material.

3. A radiometric analyzer for measuring the density, the sulfur content and calorific value of hydrocarbons by radiation comprising:
   a $\gamma$-ray absorption measuring subsystem;
   a soft X-ray absorption measuring subsystem;
   a neutron scattering measuring subsystem;
   the $\gamma$-ray absorption measuring subsystem and the soft X-ray absorption measuring subsystem each comprising a logarithmic amplifier as a linearizing circuit and the neutron scattering measuring subsystem comprising an offsettable linear amplifier as a linearizing circuit;
   a weighing adder for calculating the density of the hydrocarbons;
   a weighing adder for calculating the sulfur content per unit volume;
   a weighing adder for calculating the calorific value from the outputs of the linearizing circuits;
   a dividing circuit for dividing the output of the weighing adder for calculating the sulfur content per unit of volume, by the output of the weighing adder for calculating the density of the hydrocarbons.

4. A radiometric analyzer for measuring the characteristic values of a material by radiation comprising:
   a plurality of radiation measuring subsystems;
   the radiation measuring subsystems comprising a $\gamma$-ray subsystem, a soft X-ray subsystem and a neutron subsystem;
   the $\gamma$-ray subsystem and the soft-X-ray subsystem each comprising a logarithmic amplifier as a linearizing circuit and the neutron subsystem comprising an offsettable linear amplifier as a linearizing circuit;
   a plurality of weighing adders for calculating the characteristic values from the outputs of the logarithmic amplifiers and the offsettable linear amplifier of the subsystems.

* * * * *